United States Patent
McNeirney et al.

(10) Patent No.: US 6,267,502 B1
(45) Date of Patent: Jul. 31, 2001

(54) ALIGNMENT VERIFICATION DEVICE AND METHOD OF USING THE SAME WITH A VISUAL LIGHT BEAM AND AN X-RAY

(75) Inventors: John C. McNeirney, Fairburn, GA (US); Michael K. Landi, Kenmore; Thomas C. Koslowske, Orchard Park, both of NY (US)

(73) Assignee: Minrad Inc., Buffalo, NY (US)

( * ) Notice: Subject to any disclaimer, the term of this patent is extended or adjusted under 35 U.S.C. 154(b) by 0 days.

(21) Appl. No.: 09/087,365

(22) Filed: May 29, 1998

Related U.S. Application Data (60) Provisional application No. 60/081,396, filed on Apr. 10, 1998.

(51) Int. Cl.$^7$ .................................................. A61B 6/08
(52) U.S. Cl. ........................................... 378/206; 378/205
(58) Field of Search .................................... 378/162, 163, 378/165, 166, 205, 206, 207, 170

(56) References Cited

U.S. PATENT DOCUMENTS

| | | | |
|---|---|---|---|
| 4,061,924 | * 12/1977 | Jacoby et al. | 378/162 |
| 4,698,836 | * 10/1987 | Minasian | 378/162 |
| 5,368,030 | * 11/1994 | Zinreich et al. | 378/163 X |
| 5,848,125 | * 12/1998 | Arnett | 378/162 |

* cited by examiner

Primary Examiner—David P. Porta
(74) Attorney, Agent, or Firm—Hodgson Russ LLP (57) ABSTRACT

A device and method for verifying positional alignment between a visible light beam and an x-ray beam by providing a radio-opaque body that is to be positioned in the center of the visible light beam in the x-ray field. The image of the radio-opaque body provides an indication of whether the position of the visible light beam is colinear and coincident with the central ray of the x-ray beam of an imaging system.

20 Claims, 8 Drawing Sheets

ALIGNMENT VERIFICATION DEVICE AND METHOD OF USING THE SAME WITH A VISUAL LIGHT BEAM AND AN X-RAY

CROSS-REFERENCE TO A RELATED APPLICATION

Applicants hereby claim priority on earlier filed provisional application Ser. No. 60/081,396, filed Apr. 10, 1998, which is incorporated herein by reference.

BACKGROUND OF THE INVENTION

1. Field of the Invention

The invention relates generally to the field of aligning an x-ray and a visible light beam in a fluoroscope. More particularly, the invention relates to a device containing a radio-opaque material that provides a means to check for precise physical alignment between an x-ray in a fluoroscope and a laser beam in a laser targeting system attached to the fluoroscope.

2. Background Art

Producing and positioning a laser beam that indicates the exact surface point of entry and the precise angle of approach to a subcutaneous structure can be used in many fluoroscopically guided procedures, such as biopsies of deep tissue anatomy, screw, wire and implant placement, vertebroplasty, spinal procedures, arthrograms, selected interventional cardiology, and craniofacial and plastic surgery procedures. In these procedures the laser or other visible light beam usually serves as an accurate visible guide for accessing a subcutaneous structure. Thus, in order to correlate the position of a subcutaneous structure in an x-ray image and the point and direction of entry of a medical instrument on the skin of a patient, it is necessary to achieve the most accurate alignment of an x-ray beam with a visible light beam in a fluoroscopic machine.

The use of a visible light system together with an imaging system to mark or indicate areas of medical interest has been known in the art. For example, U.S. Pat. No. 5,031,203 to Trecha and U.S. Pat. No. 4,117,337 to Staats describe an arrangement where a patient is moved within an imaging system to a predetermined location of a laser system. A method and device for aligning x-rays and a laser beam by aligning x-rays and the bore of a cylindrical device are disclosed in U.S. Pat. No. 4,356,400 to Polizzi et al. A device for aligning a patient at the proper distance from an x-ray source by intersecting two laser beams at a predetermined position is described in British Patent No. GB 2175778A published Dec. 3, 1986. None of these patents discloses a device and method for verifying and perfecting coaxial and coincident alignment between an x-ray and a visible light beam by verifying and correcting alignment of the visible light beam within the source of the visible light beam.

U.S. Pat. Nos. 5,212,720 and 5,644,616 to Landi et al. disclose a technique that uses a calibration device with a marking made of radio-opaque material for coaxially and coincidentally aligning a laser beam with the central ray from an x-ray source.

The techniques of using a radio-opaque material as a marker to mark or encircle a particular area on an x-ray image has been known in the past. For example, U.S. Pat. No. 5,193,106 to DeSena discloses a device for providing percutaneous-based markings in association with x-ray examination procedures. The DeSena patent shows a tape having adhesive backing with a radio-opaque marker made of radio-opaque material affixed to the tape. The radio-opaque marker encloses an area of interest and serves to focus the attention of a podiatrist reviewing an x-ray photograph of the area of interest. U.S. Pat No. 5,565,678 to Manian discloses a system and methods for performing a quantative assessment of the image quality of a radiographic image. A calibration target comprising a stack of circular disks for attenuating an incident beam is employed to form a latent image and ultimately a visible radiographic image to which an examination target may be compared. U.S. Pat. No. 4,698,836 to Minasian discloses a radio-opaque movable ball disposed within a dish shaped opening. The ball is used to record position information on a patient's x-ray film. None of these patents uses a radio-opaque member to verify alignment between an x-ray and a visible light beam in a fluoroscope or any other kind of x-ray equipment. Moreover, none of these patents discloses a method and device for verifying alignment of the visible light beam in the light beam source itself.

The system of aligning an x-ray beam with a visible light beam disclosed in the Landi et al. patents comprises a visible light source with a colinearizer that are attached to an x-ray machine such as a fluoroscope. The colinearizer includes a pair of reticles mounted at each end of the colinearizer. Each reticle has radio-opaque cross-hairs that produce an image of the reticles on a x-ray image. By observing the relative position of the two pairs of cross-hairs on the x-ray image a surgeon or a bio-engineering technician can make a conclusion about the proper alignment of the visible light beam and the central ray of the x-ray beam. Such system and method, however, do not take into account the fact that the visible light beam may deflect from its intended direction inside the colinearizer when, for example, the fluoroscope is moved or when the visible light source is somehow disturbed. In the Landi et al. systems and methods the alignment of the two reticles in the colinearizer with respect to the x-ray does not solve the problem of verifying the alignment of the visible light beam inside the visible light beam source itself. The Landi et al. systems and methods presume that if the colinearizer is aligned with the x-ray beam, the visible light beam will necessarily always be properly aligned with the x-ray. That is not always so, because during the exploit of the x-ray machine the initial alignment between the reticles in the colinearizer and the visible light beam may get lost. Such loss of an alignment will inevitably cause imprecise identification of the point and direction of entry to subcutaneous structures in a patient during a medical procedure.

If a doctor could verify the alignment between the visible light beam and the x-ray as well as between the visible light beam and the source of the visible light beam itself and then print out an image corresponding to the correctly aligned equipment, the doctor would have proof of the fact that he or she operated properly functioning, precisely aligned equipment. Therefore, it would be desirable to have a device and method for verifying alignment of the direction of the visible light beam with respect to the colinearizer in addition to the alignment with respect to the direction of the central ray of the x-ray beam.

SUMMARY OF THE INVENTION

It is, therefore, a primary object of the present invention to provide a new and improved method for determining positional alignment of a visible light beam in a fluoroscopic x-ray system.

It is also an object of the present invention to provide a device and method for physically verifying the position of a visible light beam in the x-ray field of an x-ray machine.

In the alignment verification device and method of the present invention a body of radio-opaque material is incorporated into a supporting member coated or covered with an adhesive. The device can be removably attached to an image intensifier of an x-ray machine which both the x-rays and the visible light beam impinge upon. Once the general alignment between the visible light beam and the x-rays is achieved, the two reticle images will form a single superimposed reticle image on a monitor. After that the alignment verification device is placed on the image intensifier so that the visible light beam and the radio-opaque body are in direct alignment. In such an arrangement the position of the radio-opaque material indicates the place where the visible light beam hits the image intensifier. When later the visible light beam is turned off, the position of the image of the radio-opaque body in an x-ray image relative to the center of the reticle image will indicate the position of the visible light beam relative to the colinearizer, and therefore, to the x-rays. In the case of misalignment between the visible light beam and the x-rays, the visible light beam is realigned with the colinearizer and the alignment verification procedure is repeated.

These and other objects and advantages of the present invention will become increasingly more apparent to those skilled in the art by reference to the following description and to the accompanied drawings.

DETAILED DESCRIPTION OF THE PREFERRED EMBODIMENT

In the preferred embodiment the device and method of the present invention are used with C-Arm fluoroscope machines, such as the ones manufactured by OEC, Siemens, General Electric, Phillips, Toshiba and others. A system comprising a visible light source attaches to the fluoroscope. An example of a system with a visible light source suitable for use with a C-Arm fluoroscope is the Dual Radiation Targeting System (DRTS™) platform described in U.S. Pat. Nos. 5,212,720 and 5,644,616 to Landi et al., which patents are incorporated herein by reference.

Figure 1:
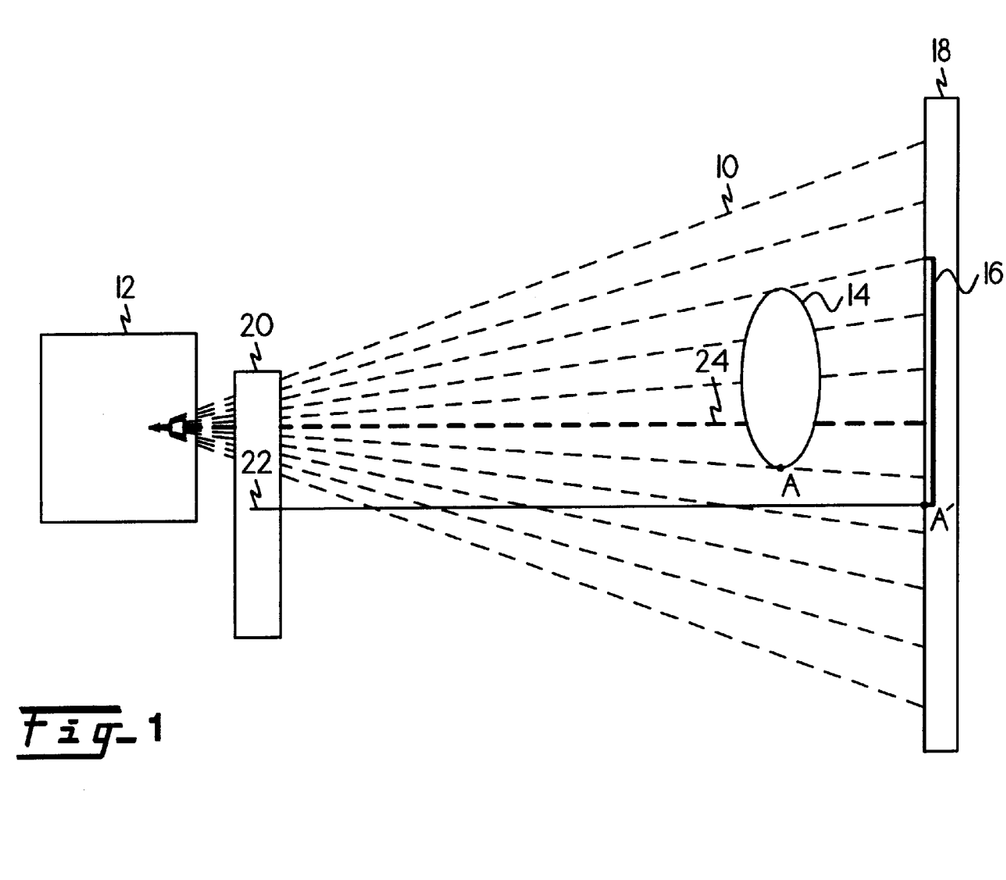
FIG. 1 is a schematic representation of non-aligned visible light beam and x-rays in an x-ray machine.
Figure 2:
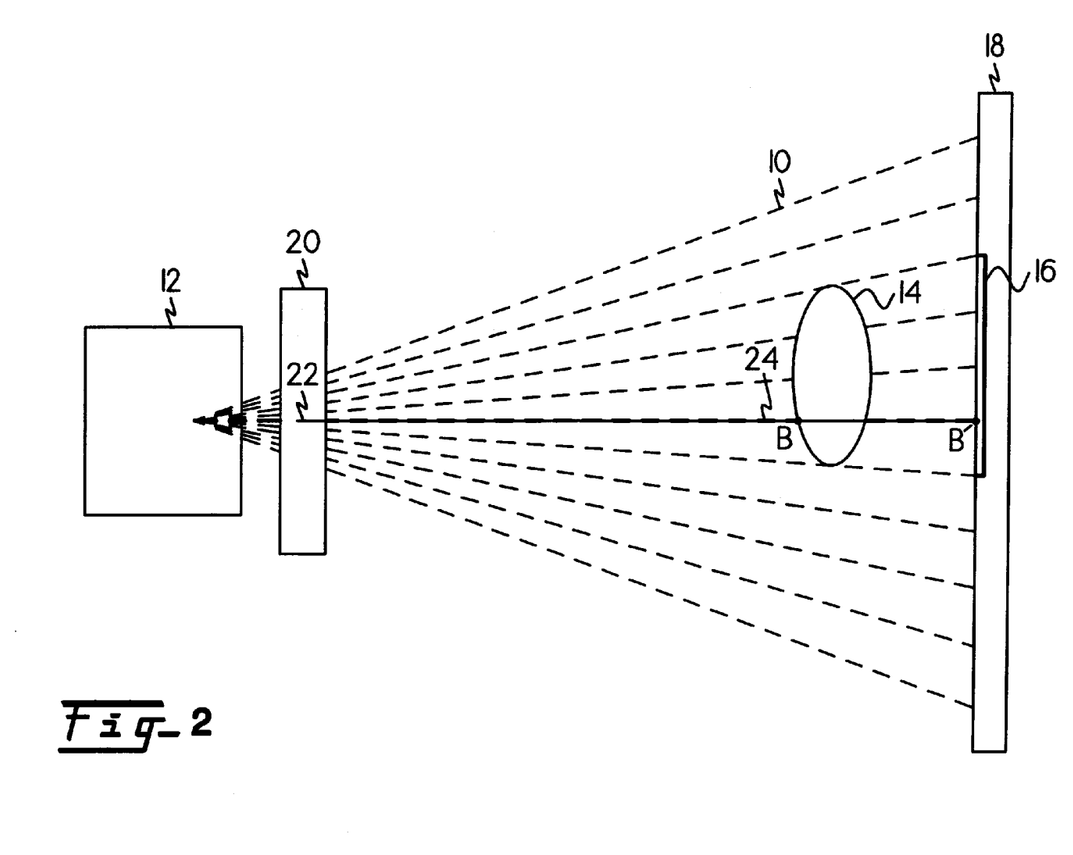
FIG. 2 is a schematic representation of aligned visible light beam and x-rays in an x-ray machine.
Figure 3A:
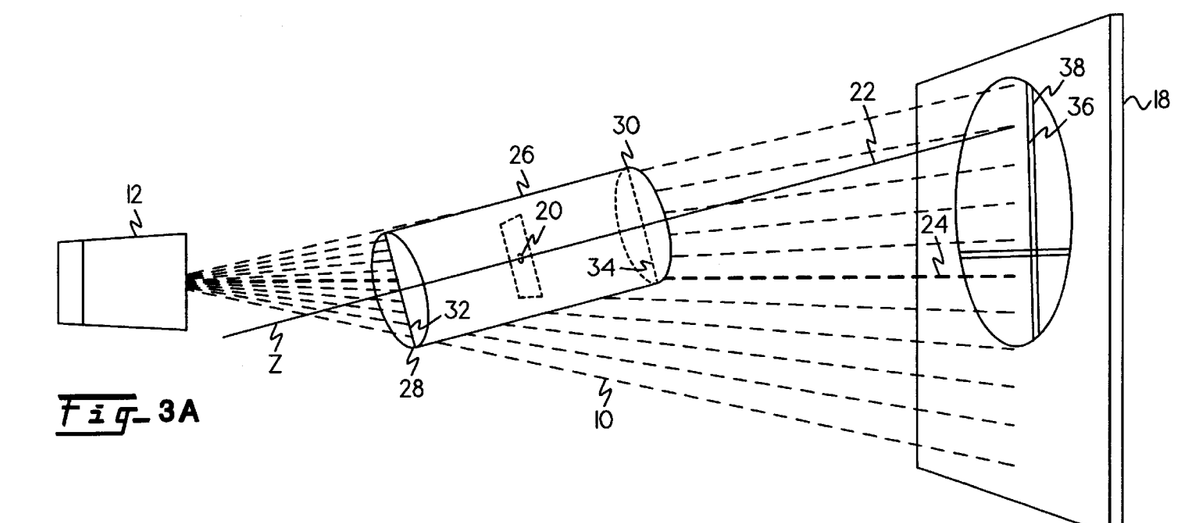
FIG. 3A is a schematic representation of non-aligned colinearizer and x-rays.
Figure 3B:
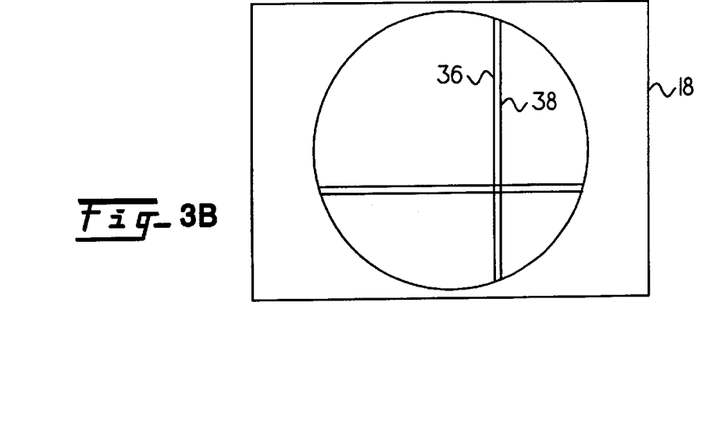
FIG. 3B is an image formed by cross-hairs of two reticles when the colinearizer is not aligned with the x-rays.
Figures 3C, 3D:
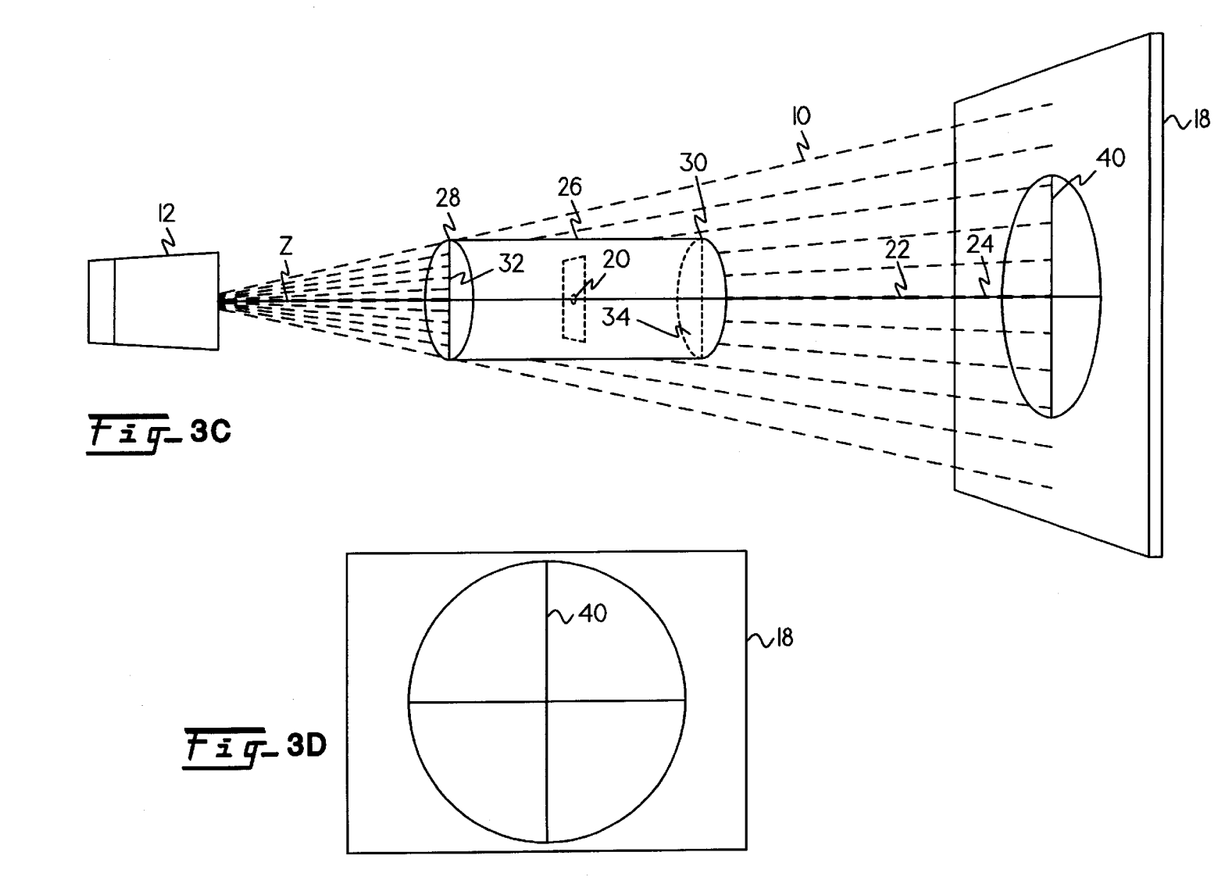
FIG. 3C is a schematic representation of aligned colinearizer and x-rays.
FIG. 3D is a superimposed image formed by cross-hairs of two reticles when the colinearizer is aligned with the x-rays.

As illustrated in FIG. 1, in an x-ray/visible light beam imaging system x-rays 10 exit an x-ray source 12 of a fluoroscope in a conical array. As the x-rays pass through a target 14, they form an image 16 of target 14 on a monitor 18. A visible light source 20 that is attached to the fluoroscope generates a visible light beam 22. As shown in FIG. 1, visible light beam 22 and a central x-ray 24 are coaxially and coincidentally unaligned. Because beam 22 and central x-ray 24 are unaligned, point $A^1$ of image 16 on monitor 18 appears to be the point of entry at which beam 22 impinges upon image 16. However, point A of target 14 that corresponds to point $A^1$ of image 16 is not the point of entry of beam 22, as illustrated in FIG. 1. Therefore, when beam 22 and central x-ray 24 are unaligned, the information of the relative positions of target 14 and beam 22 provided by image 16 is incorrect. If beam 22 and central x-ray 24 are coaxially and coincidentally aligned, as illustrated in FIG. 2, then the point of entry B on target 14 correctly corresponds to the point of entry $B^1$ on image 16 formed on monitor 18. In order to coaxially and coincidentally align beam 22 and central x-ray 24 the DRTS™ platform utilizes a visible light source 20 that generates visible light beam 22 along a central axis Z of a colinearizer 26, as shown in FIG. 3A. A pair of reticles 28 and 30 are inserted at each end of colinearizer 26. Each reticle has radio-opaque cross-hairs 32 and 34 marked on the reticles. When axis Z of colinearizer 26 is not aligned with central x-ray 24 of the array of x-rays 10, radio-opaque cross-hairs 32 and 34 will produce two separate unaligned reticle images 36 and 38 on monitor 18, as illustrated in FIG. 3B. Therefore visible light beam 22 is also unaligned with central x-ray 24. However, when axis Z of colinearizer 26 is colinear with central x-ray 24 of the array of x-rays 10, as shown in FIG. 3C, the images of two radio-opaque cross-hairs will superimpose, forming a single reticle image 40 on monitor 18, as illustrated in FIG. 3D. Therefore, when a surgeon or a medical technician observes two reticle images on monitor 18, he or she will be able to correct the position of visible light beam source 12 so that the two images superimpose and form a single reticle image 40.

Figure 4:
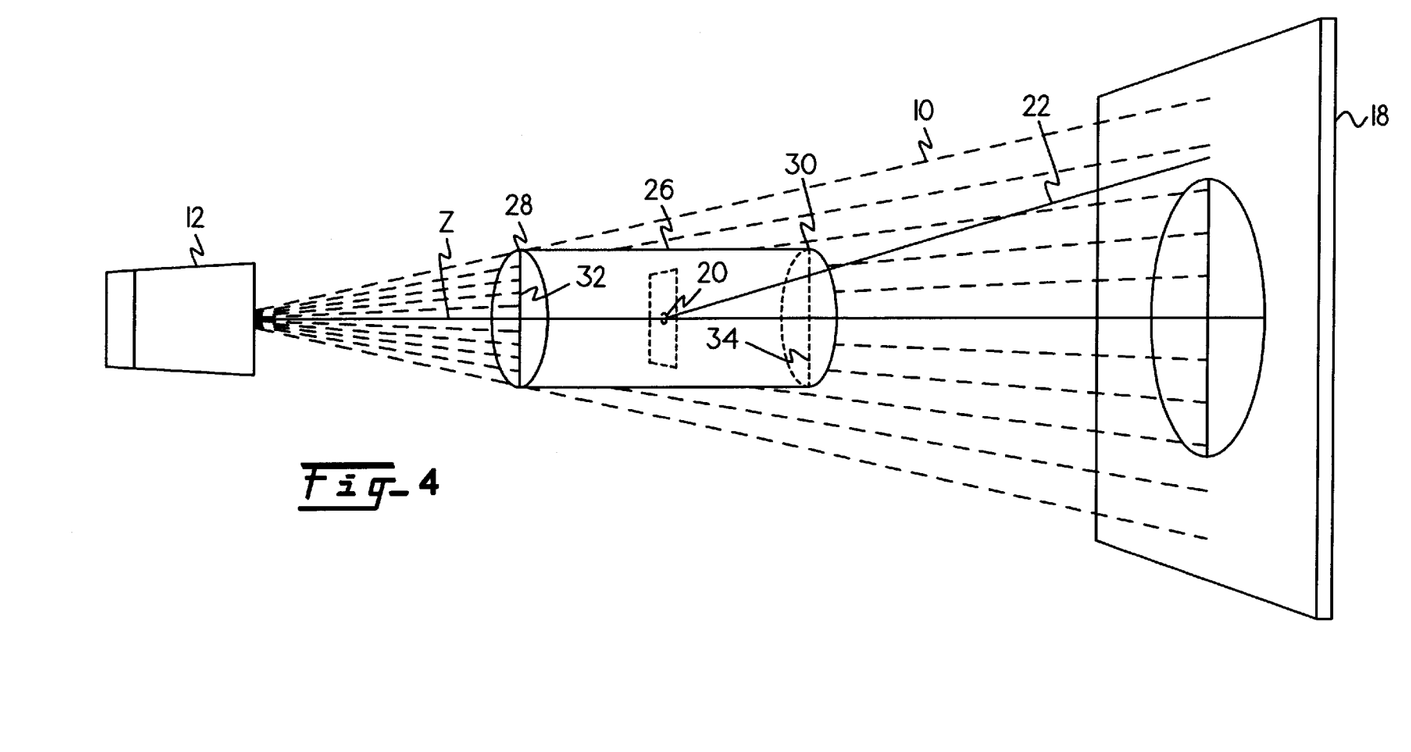
FIG. 4 is a schematic representation of misalignment between a visible light beam and a colinearizer.

The above-described alignment mechanism provides correct alignment only when the direction of visible light beam 22 coincides with the direction of axis Z of colinearizer 26. If for any reason the direction of visible light beam 22 is not coaxial with axis Z of colinearizer 26, then a single reticle image 40 of superimposed radio-opaque cross-hairs will not be indicative of visible light beam 22 being coaxially aligned with central x-ray 24, as shown in FIG. 4. Indeed, as illustrated in FIG. 4, axis Z of colinearizer 26 and central x-ray 24 are coaxial, but visible light beam 22 is not coaxial with central x-ray 24 even thought a single superimposed image 40 of two reticles will indicate, falsely in this case, proper alignment between visible light beam 22 and central x-ray 24.

Figure 5A:
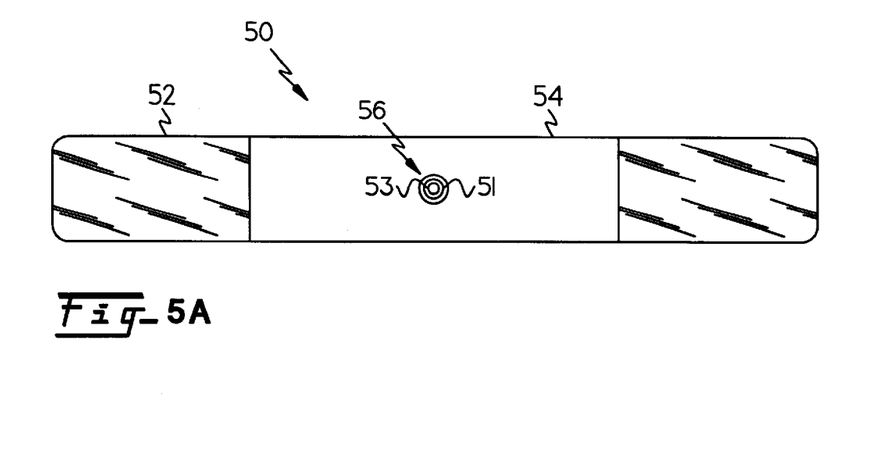
FIG. 5A is a top view of an alignment verification device of the present invention.
Figure 5B:
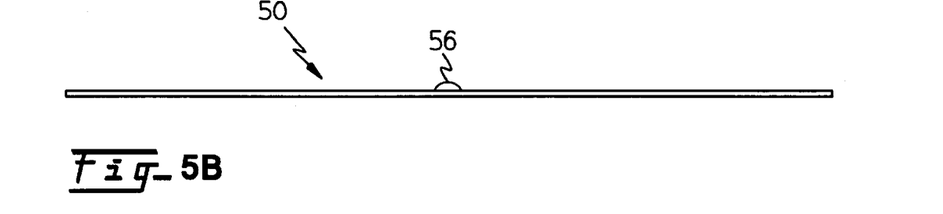
FIG. 5B is a side view of the alignment verification device of the present invention.
Figure 5C:
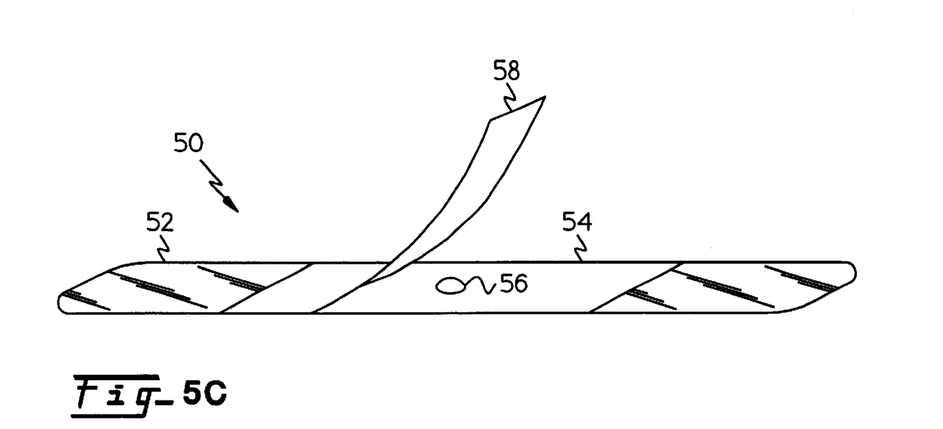
FIG. 5C is a perspective view of the alignment verification device with a peel-off covering.

The alignment verification device of the present invention is used to check the accuracy of the actual alignment between visible light beam 22 and central x-ray 24. One of the embodiments of the alignment verification device of the present invention is illustrated in FIG. 5A. The embodiment shows a device 50 comprising a supporting member 52 capable of attaching device 50 to a surface that is impinged upon by visible light beam 22 (not shown). In the preferred embodiment of the present invention supporting member 52 is in the form of a strip, a part 54 of which is covered by an adhesive for attaching member 52 to an x-ray machine. In the preferred embodiment strip 52 can be made of a transparent plastic material. Additionally, the preferred embodiment contemplates that part 54 which is covered or coated with the adhesive is also covered by a removable peel-off covering 58, as illustrated in FIG. 5C.

Supporting member 52 incorporates into it a three-dimensional radio-opaque body 56 which is permanently attached to supporting member 52. In the preferred embodiment of the present invention three-dimensional radio-opaque body 56 is a spherically shaped member made of lead located in the center of a strip-like supporting member 52, as illustrated in FIGS. 5A, 5B and 5C. It is contemplated by the present invention that three-dimensional radio-opaque body 56 can be made of any radio-opaque material. The diameter of the spherically shaped member preferably is within the range of 0.5 mm to 2 mm. Strip-like supporting member 52 is preferably from 2 cm to 20 cm long and from 0.5 cm to 5 cm wide. It is also preferable that part 54 comprises a plurality of circles (51 and 53 in FIG. 5A) that help a person to align visible light beam 22 and radio-opaque body 56. Furthermore, the preferred embodiment of the present invention calls for the diameter of the spherically shaped member to be comparable to the cross-section of visible light beam 22 to facilitate a person aligning light beam 22 with body 56.

Figure 6:
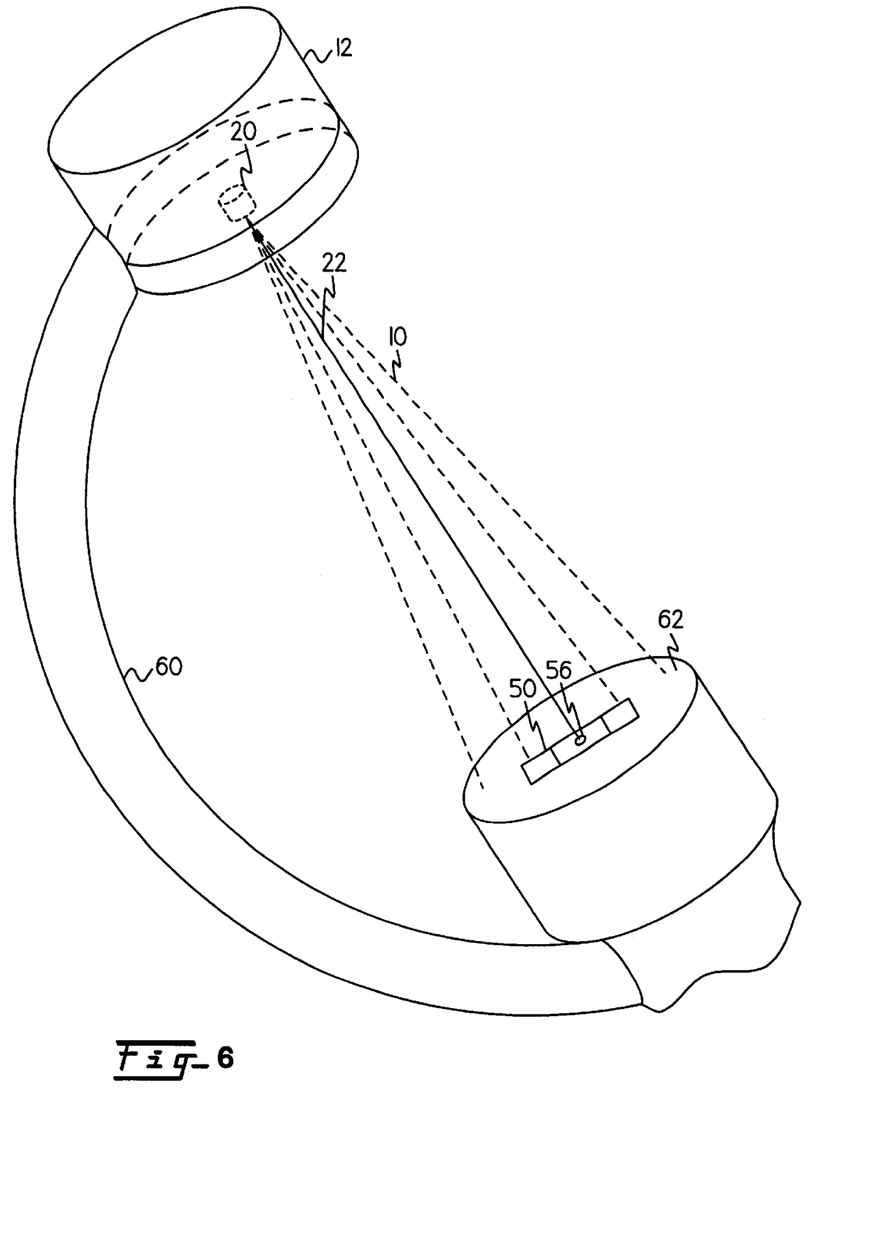
FIG. 6 is a schematic representation of an x-ray machine as used with the alignment verification device.

Alignment verification device 50 of the present invention calls for the following procedure of achieving verification of alignment of visible light beam 22 from visible light beam source 20 and central x-ray 24, as shown in FIG. 6. With conical array of x-ray 10 turned on in an x-ray machine 60, visible light beam 22 is aligned with central x-ray 24 by aligning colinearizer 26 and central x-ray 24 using reticles 28 and 30 to obtain a single superimposed reticle image like image 40, as described above in connection with FIGS. 3C and 3D. Once colinearizer 26 and central x-ray 24 are in alignment, x-ray 10 is turned off and visible light beam 22 is turned on. After that alignment verification device 50 of the present invention is attached to image intensifier 62 of x-ray machine 60 so that three-dimensional radio-opaque member 56 is in direct alignment with visible light beam 22, as illustrated in FIG. 6.

Figure 7A:
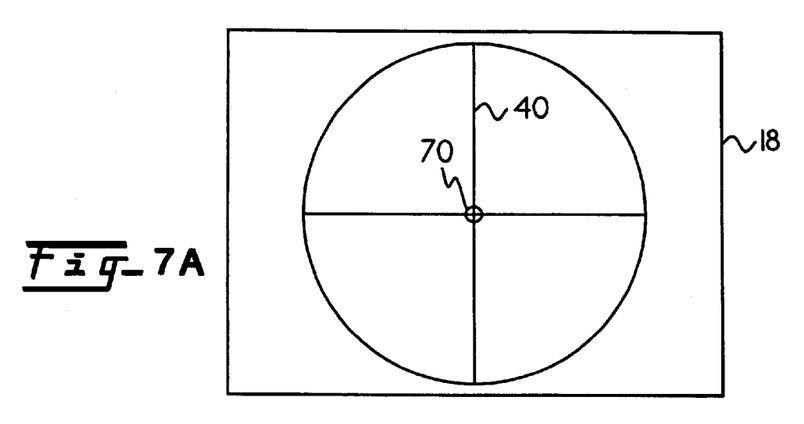
FIG. 7A is a representation of an image corresponding to precise alignment between a visible light beam and x-rays.
Figure 7B:
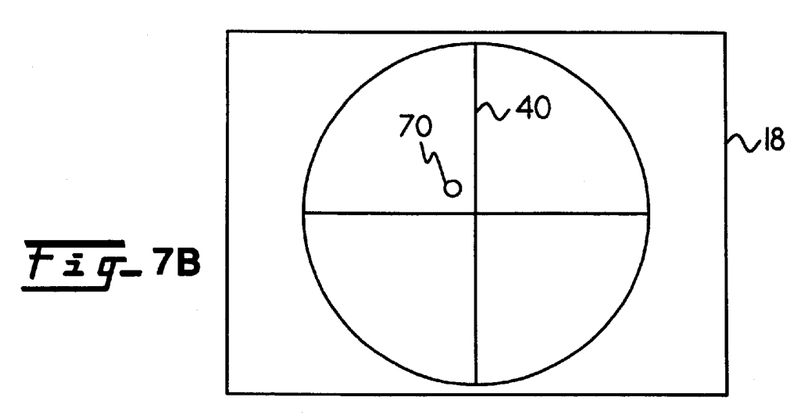
FIG. 7B is a representation of an image corresponding to misalignment between the visible light beam and the x-rays.

With x-ray 10 turned on again and visible light beam 22 off, a user then observes a position of an image 70 of three-dimensional radio-opaque member 56 in an x-ray image on monitor 18 relative to the center of aligned superimposed reticles 40, as illustrated in FIGS. 7A and 7B. If image 70 coincides with the intersection of radio-opaque cross-hairs of aligned superimposed reticles 40 on monitor 18, as shown in FIG. 7A, it means that visible light beam 22 and central x-ray 24 are indeed in alignment. If, on the other hand, image 70 does not fall in the intersection of aligned superimposed reticles 40, as illustrated in FIG. 7B, it means that visible light beam 22 and colinearizer 26 are misaligned and that actual alignment between visible light beam 22 and central x-ray 24 has not been achieved. In that case directions of visible light beam 22 and central x-ray 24 are adjusted relative to each other and their alignment is verified again in accordance with the method of the present invention described above.

It should be noted that even though the visible light beam described above can be any collimated visible light beam, in the preferred embodiment of the present invention the visible light beam is a laser beam.

It is appreciated that various modifications to the inventive concept described herein may be apparent to those of ordinary skill in the art without departing from the spirit and scope of the present invention as defined by the appended claims.

What is claimed is:

1. A method of aligning a visible light beam with an x-ray, comprising the steps of:
   providing a radio-opaque body;
   directing the visual light beam along a beam axis from a source to a surface that will be irradiated by the x-ray;
   placing the radio-opaque body on the surface so that the beam axis and the center of the radio-opaque body are in alignment;
   turning the x-ray on so that the x-ray is directed along an x-ray axis to the surface;
   observing a visual location of the image of the radio-opaque body in an x-ray image; and
   utilizing the image of the radio-opaque body in the x-ray image to determine the relative directions of the beam axis and the x-ray axis so that the proper alignment can be made.

2. The method of claim 1 further comprising a step of turning the visible light beam off before the step of turning the x-ray on.

3. The method of claim 1, wherein the visible light beam is a laser beam.

4. The method of claim 1, wherein the radio-opaque body is carried by a supporting member.

5. The method of claim 1, wherein the radio-opaque body is spherically shaped.

6. The method of claim 1, wherein the radio-opaque body is made of lead.

7. The method of claim 1 further including comprising the step of adjusting relative locations of the visible light beam and the x-ray proper alignment therebetween.

8. The method of claim 1, wherein a diameter of the radio-opaque body and a cross-section of the visible light beam are substantially the same.

9. A method of aligning a visible light beam with an x-ray for use with an apparatus comprising a monitor and an optical system having a radio-opaque marking, the method comprising the steps of:
   providing a radio-opaque body;
   directing the visual light beam along a beam axis from a source to a surface that will be irradiated by the x-ray;
   placing the radio-opaque body on the surface so that the beam axis and the center of the radio-opaque body are in alignment;
   turning the x-ray on so that the x-ray is directed along an x-ray axis of the surface;
   observing a visual location of the image of the radio-opaque body relatively to the image of the radio-opaque marking in an x-ray image generated on the monitor; and
   utilizing the image of the radio-opaque body and the image of the radio-opaque marking to determine the relative directions of the beam axis and the x-ray axis so that the proper alignment can be made.

10. The method of claim 9 further comprising a step of turning the visible light beam off before the step of turning the x-ray on.

11. The method of claim 9, wherein the visible light beam is a laser beam.

12. The method of claim 9, wherein the radio-opaque body is carried by a supporting member.

13. The method of claim 9, wherein the radio-opaque body is spherically shaped.

14. The method of claim 9, wherein the radio-opaque body is made of lead.

15. The method of claim 9, wherein the optical system comprises two reticles.

16. The method of claim 15, wherein the radio-opaque marking comprises cross hairs on each reticle.

17. The method of claim 9 further including comprising the step of adjusting relative locations of the visible light beam and the x-ray proper alignment therebetween.

18. The method of claim 13, wherein a diameter of the radio-opaque body and a cross-section of the visible light beam are substantially the same.

19. An arrangement for aligning a visible light beam and an x-ray beam which beams will be incident on a surface, the arrangement comprising:
   a) means for defining the surface on which the beams will be incident;
   b) an x-ray source for providing an x-ray beam directed along an x-ray axis to the surface;
   c) a visible light beam source for providing a visible light beam directed along a light beam axis to the surface; and
   d) a device for aligning the visible light beam and the x-ray beam comprising a supporting member having attachment means on one side attaching the side to the surface and a three-dimensional body of radio-opaque material carried by the supporting member so that when the three-dimensional body is in direct alignment with the visible light beam, an x-ray image thereof can be used to determine the relative directions of the beams and make proper alignment.

20. The arrangement according to claim 19, wherein the x-ray source is a fluoroscope, the means for defining the surface is a target operatively associated with the fluoroscope and the visible light beam source provides a collimated visible light beam.

* * * * *